United States Patent
Soler Monente et al.

(10) Patent No.: US 12,265,282 B2
(45) Date of Patent: Apr. 1, 2025

(54) METHOD TO ESTABLISH THE SIZE OF THE DIFFERENT AREAS OF A PROGRESSIVE LENS

(71) Applicant: HORIZONS OPTICAL, S.L.U., Barcelona (ES)

(72) Inventors: Santiago Soler Monente, Madrid (ES); Pau Artús Colomer, Barcelona (ES); Glòria Casanellas Peñalver, Barcelona (ES); Rocío B. Rodríguez Domínguez, Barcelona (ES); Javier Vegas Caballero, Barcelona (ES)

(73) Assignee: HORIZONS OPTICAL, S.L.U., Barcelona (ES)

( * ) Notice: Subject to any disclaimer, the term of this patent is extended or adjusted under 35 U.S.C. 154(b) by 483 days.

(21) Appl. No.: 17/714,394

(22) Filed: Apr. 6, 2022

(65) Prior Publication Data
US 2022/0326543 A1    Oct. 13, 2022

(30) Foreign Application Priority Data
Apr. 6, 2021    (EP) .................................. 21382289

(51) Int. Cl.
G02C 7/02       (2006.01)
A61B 3/113      (2006.01)
G02C 7/06       (2006.01)

(52) U.S. Cl.
CPC .............. *G02C 7/027* (2013.01); *A61B 3/113* (2013.01); *G02C 7/066* (2013.01)

(58) Field of Classification Search
CPC ........ G02C 7/027; G02C 7/066; G02C 7/028; G02C 7/025; A61B 3/113
(Continued)

(56) References Cited

U.S. PATENT DOCUMENTS 8,322,855 B2    12/2012  Giménez Carol et al.
10,371,948 B2*   8/2019  Samec .................. G16H 20/17
(Continued)

FOREIGN PATENT DOCUMENTS

ES    2264848 B1      1/2008
WO    2020074566 A1   4/2020

OTHER PUBLICATIONS

Gloria Casanellas Penalver, "Optimization methods for the design of progressive lenses", Doctoral Thesis, Department of Statistics and Operations Research, Universitat Politecnica de Catalunya—BarcelonaTech, Mar. 5, 2020. Barcelona, Spain. (135 pages).

(Continued)

*Primary Examiner* — Tuyen Tra
(74) *Attorney, Agent, or Firm* — Amster, Rothstein & Ebenstein LLP (57) ABSTRACT

Method to establish the size of the zones of near $A_c$, far $A_L$ and intermediate $A_i$ vision of a progressive lens by generating, thanks to virtual reality, a gaze map of the user while following a stimulus in at least two planes at two different distances. Once the gaze maps have been made in those two planes or more, the area of each zone is calculated from the maximum horizontal and vertical amplitudes and the points of maximum frequency. In this way, the lens is adapted to the way a user looks.

6 Claims, 5 Drawing Sheets

(58) Field of Classification Search
    USPC .................. 351/41, 159.01, 159.41, 159.42
    See application file for complete search history.

(56) References Cited

U.S. PATENT DOCUMENTS 11,922,517 B2 * 3/2024 Jain .......................... H04L 63/08
2020/0098184 A1 3/2020 Lo et al.

OTHER PUBLICATIONS

G. Casanellas and P. Artus, "Do the progressive lenses really satisfy the Minkwitz theorem? Strategies to go beyond the Minkwitz theorem." Innovation Department of Horizons Optical, MAFO—Ophthalmic Labs & Industry, vol. 15, pp. 10-17, Jan. 2019. ISSN 1614-1598 66527.
Essilor USA, "Visioffice and Varilux S Series Measurement Explanations" (https://www.essilorusa.com/content/dam/essilor-redesign/visioffice/Visioffice%20Measurement%20FAQ.pdf). Updated Dec. 2012. (8 pages).
European Patent Office, Extended European Search Report and Written Opinion issued in Application No. EP 22382313, dated Aug. 4, 2022. Munich, Germany. (9 pages).

* cited by examiner

METHOD TO ESTABLISH THE SIZE OF THE DIFFERENT AREAS OF A PROGRESSIVE LENS

CROSS-REFERENCE TO RELATED APPLICATION

This application claims priority, pursuant to 35 U.S.C. § 119, to European Patent Application No. 21382289.3, filed Apr. 6, 2021, the contents of which are incorporated herein by reference in their entirety.

TECHNICAL SECTOR

The present invention is encompassed within optical applications in particular, progressive lenses.

BACKGROUND OF THE INVENTION

Figure 1:
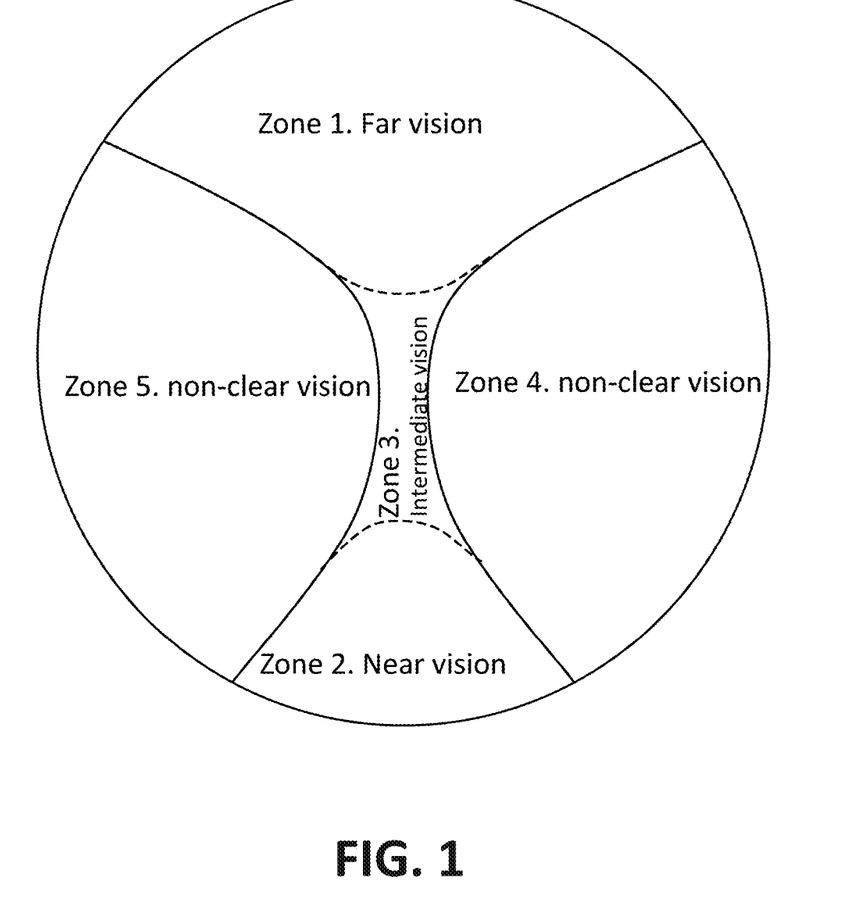
FIG. 1: schematic representation of the zones of a progressive lens.

A progressive lens has three distinct clear areas with different optical powers that allow objects to be focused at different distances: far, intermediate and near. There is a fourth and fifth non-clear areas, located on the sides, where aberrations inevitably appear, causing a lower optical quality (see FIG. 1). This makes it difficult to use when looking through them.

It is known that multipurpose progressive lenses are characterized by being designed to have an upper zone of focus on objects located at a far distance of 5 meters or more, another in the lower part to focus on objects around 40 cm away, and a third in the central zone with progressively changing focus capacity from near to far distance, called intermediate zone or corridor.

Due to the progressive power variation of this intermediate zone, the sides of these lenses always have aberrations that do not allow the user to focus precisely. This is due to the fact that unwanted astigmatism appears with values greater than 0.50 Diopters, which is the limit value from which the human eye-brain group begins to have a perception of lack of clarity (see FIG. 2).

Consequently, the clear zone of far vision of a progressive lens is defined as the area where the astigmatism value is less than 0.50 Diopters and the mean power value is less than +0.25 Diopters of the far target power value. In the upper part, the area is limited to 8 millimeters above the position of the pupil (known as the fitting cross or segment) while at the bottom it is limited to 4 mm below the position of the pupil, which usually coincides with the point known as the prism reference point (PRP)

The clear zone of near vision of a progressive lens is defined as the area where the astigmatism value is less than 0.50 Diopters and the mean power value is greater than 85% of the near average power, which takes into account the addition. At the upper part, this limit is usually about 4 mm above the near reference point (known as the Near Reference Point or NRP). At the bottom, the near area is limited to 2 millimeters below the near reference point (known as the Near Reference Point or NRP).

The clear zone of intermediate vision of a progressive lens is also defined as the area where the astigmatism value is less than 0.50 Diopters and the power varies continuously from +0.25 Diopters of the objective value from far to 85% of the value of the addition. At the upper part, it is limited above the PRP, while the bottom is usually limited to about 4 mm above the NRP. The corridor is defined as the vertical length of the clear zone of intermediate vision.

Figure 2:
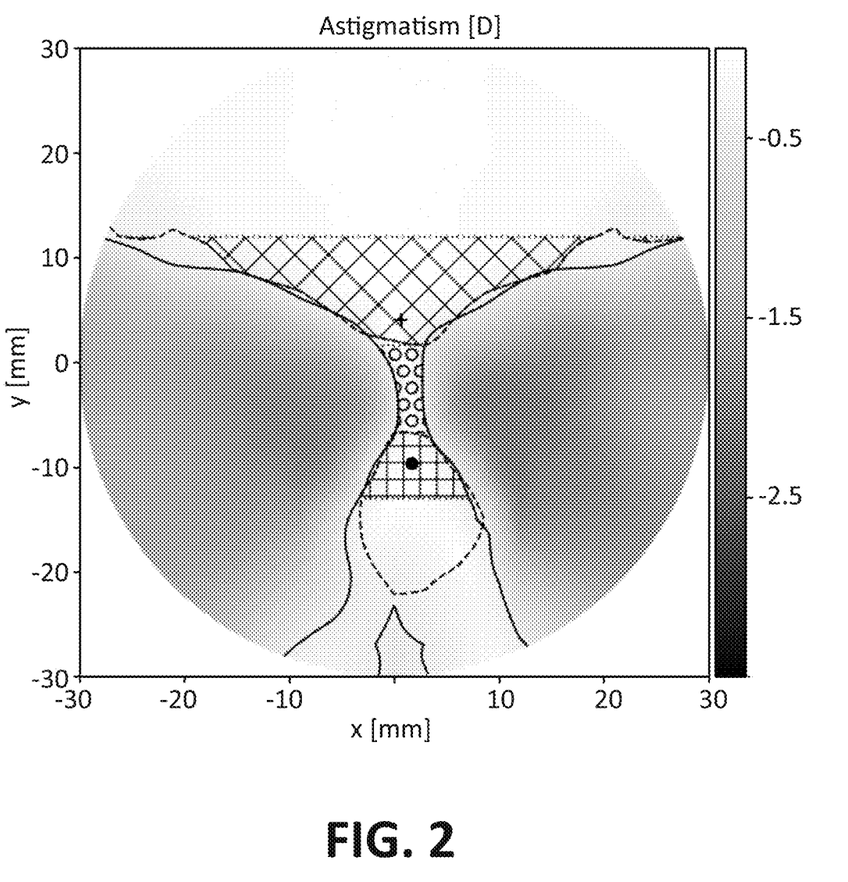
FIG. 2: graphical representation of the areas of a progressive lens calculated from the astigmatism and addition values (diamonds: far vision zone; circles: intermediate vision zone; squares: near vision zone; gray: zones 4 and 5 without clear vision). The cross shows the location of the fitting cross point. The dot shows the location of the NRP.

An example of a combined astigmatism and mean power map of a progressive lens is shown in FIG. 2 with each of the three useful zones 1-3 marked, and also zones 4 and 5 not having clear vision.

It is known that for the calculation of progressive lenses, iterative optimization methods are used that incorporate as restrictions the values of power and astigmatism required in each zone described ("Optimization methods for the design of progressive lenses", Casanellas, Glòria. Universitat Politècnica de Catalunya, 2020. http://hdl.handle.net/10803/668877). These mathematical methods iteratively modulate the lens surface, being understood as two surfaces containing a material of known refractive index, until the objective function requirements are met within specified tolerances for each point.

It is also known that the size and distribution of each of the zones (far, intermediate, near and aberrations) does not have a unique mathematical solution, so it is possible to modify them within certain limits ("Do the progressive lenses really satisfy the Minkwitz theorem? Strategies to go beyond the Minkwitz theorem." Innovation Department of Horizons Optical. MAFO—Ophthalmic Labs & Industry, Volume 15, pp 10-17, January/2019. ISSN 1614-1598 66527).

Consequently, there may be many possible geometries to define the contour of each of the zones once their size is established. A known model is the one constituted by polyhedrons that define the limits of the zones and that can be used for the mathematical definition of the optimization system. Specifically, one of the simplest models uses two trapezoids to define the contours of the far and near zone, and a rectangle or parallelogram for the intermediate zone, depending on whether a symmetric or asymmetric progressive lens is designed. There are also more sophisticated models in which one or more of the edges of the polyhedrons are replaced by arcs of circumference, arcs of ellipses or n degree polynomials.

A progressive lens with larger areas for near and far focus causes the fourth and fifth zones to be smaller but have high levels of aberration and image distortion. This often causes a greater difficulty in adapting to especially sensitive users. This is the case of progressive lens designs commonly known as hard.

On the contrary, an expansion of the fourth and fifth zones entails a more limited intensity of aberrations on the sides and an intermediate zone with a wider transition corridor or corridor. These types of lenses usually offer easier adaptations for some users but others do not prefer them, since they cause a greater sensation of visual restriction on the sides of far, near areas and corridor. This is the case of progressive lens designs commonly known as soft.

The location and size of these areas, especially those that are not clear, conditions the users oculomotor movement since, for different gaze directions, users prefer to prioritize head movement over ocular rotation or vice versa, depending on the intensity of the aberrations and the sensitivity of each user to them.

The a priori preference of a user over progressive lenses with different area sizes, without having tried them, is one of the challenges that the ophthalmic lens sector has been pursuing since the beginning of progressive lenses. For this reason, many lens manufacturers have diagnostic tests and devices that aim to improve the characterization of the users in order to objectify the sensations in perception and to be able to better adjust the selection of the designed or chosen lens.

For some years there have been devices on the market that attempt to measure the behavior of users and record head and eye movements with the aim of improving the prescribed progressive lenses. Some examples would be:

Visioffice from Essilor (https://www.essilorusa.com/content/dam/essilor-redesign/visioffice/Visioffice%20Measurement%20FAQ.pdf): this device measures various parameters relevant to the optician and incorporates the measurement of the percentage of eye moving/head moving on the horizontal axis from a simple one-dimensional test with a light stimulus of two LEDs located on each side of the user. There is also a more specific device from the same company called Varilux® VisionPrint System™ (http://www.luzerne-optical.com/pdf/varilux-physio-faqs.pdf) that follows the same principle.

Patent ES2264848; describes a method for measuring the visual map of the user from the tracking of the users eyes and head while following a punctual light stimulus moving on a two-dimensional black screen.

Virtual reality is a stereoscopic simulation of reality both visually and audibly, its main characteristic being the ability to provide an immersion of the subject in a three-dimensional and, consequently, multisensory environment.

Unlike desktop or floor-standing equipment that is limited by the space it occupies and by the hardware, a virtual reality environment allows you to create scenarios specially designed for each test in which you want to record the dynamics of your gaze. The lighting conditions are controlled, and the experience is completely immersive, with which the results are more repetitive and there are no distractions or unforeseen events, resulting in an ideal experience for conducting tests related to the health world.

For example, there are many applications for training purposes for health professionals that allow simulating work environments and critical situations to help improve their reactions.

Currently available virtual reality devices have a level of precision in determining the position of the head that makes them especially effective in determining the movement of the head. They incorporate inertial sensors of the accelerometer and gyroscope type to determine the movements of the head and synchronize the movement of the virtual environment appropriately. Optionally, some devices can also incorporate pupil movement sensors (eye-tracker), which completes the information on the users oculomotor movement. To create the stereoscopic sensation in the user, virtual reality devices project complementary images to each eye that place the objects in the relative position with respect to the background based on the calculated position in space.

The gaze dynamics map is known as the record of the positions in the users gaze while carrying out certain activities. To determine the gaze dynamic's map of each person, it is necessary to project a stimulus in the virtual space that the user is asked to follow naturally with his gaze. The virtual reality device will record the relative movement of the eyes and head to determine the frequency of use of each area of the plane where an ophthalmic lens would be located. This recording is made while the patient is asked to follow with his gaze a stimulus that is moving freely in the three dimensions of the virtual space.

In the event that the device lacks an eye-tracker, a simplification can be used assuming that the patient always faithfully follows the stimulus. This simplification is especially suitable for patients with dysfunctions in the visual system such as phoria, amblyopia or nystagmus since the tracking devices do not give a reliable answer on the real direction of the gaze.

In the case of knowing the gaze dynamics of each specific user at each distance, it is possible to adapt the size of each area of the lens to their needs and type of gaze dynamics, providing a unique and exclusive lens perfectly adapted to their way of viewing.

Additionally, the position of the near zone of a progressive lens can be adjusted vertically so that it is positioned in a comfortable position for the user when performing near and intermediate vision tasks. This change in location determines the vertical length of the intermediate vision zone, which is usually called the corridor, and consequently, the size and intensity of the lateral aberrations since the intensity of the variation of optical power in this corridor is also interrelated with the level of aberrations (shorter corridors have higher level of lateral aberrations).

Additionally, if the progressive lens to be manufactured is not a multipurpose lens and is designed to be an occupational lens, said object focus distances will be different. For example, for an office lens the power will be adapted for the far distance to focus between 1.5 and 3 m instead of the 5 m or more usual ones. In contrast, for a lens for outdoor sports activities, the near distance would be optimized for focusing on the ground and would be between 1.5 and 2 m, instead of the usual 40 cm for reading.

SUMMARY OF THE INVENTION

In order to physically manufacture a progressive lens adapted to the way a person looks, the present invention describes the method for determining and calculating the size of the far, near and intermediate areas of said lens from the measurement of the dynamics of the patient's gaze. Gaze dynamics maps are obtained using a virtual reality environment within which stimuli are projected in at least two planes at at least two different distances: far and near, and recording their eye and head movement and the calculation is done by means of processing.

The size of the far vision area ($A_L$) in $mm^2$ of the progressive lens will be determined from the average of the maximum horizontal and vertical amplitude of the gaze dynamics map in the far plane ($\Delta ab_L$), expressed in degrees (°), following a linear relationship for $\Delta ab_L$ values between 10° and 80° according to the following relationship:

$$A_L = i \times \Delta ab_L + j,$$

wherein i values are between 1.0 $mm^2/°$ and 1.4 $mm^2/°$, preferably 1.2 $mm^2/°$ and j has values between 120 $mm^2$ and 160 $mm^2$, preferably 140 $mm^2$.

The size of the near vision area ($A_C$) in $mm^2$ of the progressive lens will be determined from the average of the maximum horizontal and vertical amplitude of the gaze dynamics map in the near plane ($\Delta ab_C$), expressed in degrees (°), following a linear relationship for $\Delta ab_C$ values between 10° and 80° according to the following relationship:

$$A_C = k \times \Delta ab_C + l$$

wherein k has values between 0.15 $mm^2/°$ and 0.25 $mm^2/°$, preferably 0.20 $mm^2/°$ and wherein l has values between 20 $mm^2$ and 30 $mm^2$, preferably 25 $mm^2$.

The size of the intermediate vision area ($A_I$) in $mm^2$ of the progressive lens will be determined from the angle formed by the $PM_L$ and $PM_C$ points with the origin of coordinates ($\beta PM_{LC}$), expressed in degrees (°), following a linear relationship for $\beta PM_{LC}$ values between 0° and 18° according to the following relationship:

$A_I = m \times \beta PM_{LC} + n$ wherein m has values between 0.5 mm²/° and 1.5 mm²/°, preferably 1.0 mm²/° and n has values between 15 mm² and 30 mm², preferably 23 mm².

BRIEF DESCRIPTION OF THE FIGURES

In order to help a better understanding of the features of the invention and to complement this description, the following figures are attached as an integral part thereof, the nature of which is illustrative and not limiting.

DETAILED DESCRIPTION

For each user, the following sequence of steps is followed:
1. Protocol to ensure the correct fit of a virtual reality glasses to the users head (adjustment of fastening straps, correct position of the glasses in front of the eyes, etc.).
2. Transfer of the patient to the virtual space where the test will be performed. It is a relaxed and distraction-free environment.
3. Preparation of the patient to ensure a natural position of the back and neck.
4. The patient is asked to look at infinity and the tilt of the head relative to the ground is recorded as their Resting Position and the patient's gaze direction relative to the ground as the Direction of Rest ($D_R$).
5. A Cartesian coordinate system is defined with the origin (0,0,0) at the midpoint of the vector joining the users pupils. The xy plane is defined parallel to the ground and the z axis perpendicular to the ground. A vector is defined that has the origin of the coordinate system as its origin and has the direction of rest ($D_R$) as its direction. It is defined that the xz plane contains this vector
6. The Far Zone is defined as the portion of the plane parallel to yz with a value of x corresponding to the far distance for which the Far Area ($A_L$) of the progressive lens is to be adjusted (for example, 5 meters or more for a multipurpose progressive lens) and having a horizontal size of at least 100° and a vertical size of at least 80°. These angles are measured from the origin of coordinates (0 m, 0 m, 0 m).
7. The Near Zone is defined as the portion of the plane parallel to yz with a value of x corresponding to the near distance for which the Near Area ($A_C$) of the progressive lens is to be adjusted (for example, 0.4 meters for a multipurpose progressive lens) and having a horizontal size of at least 100° and a vertical size of at least 80°. These angles are measured from the origin of coordinates (0 m, 0 m, 0 m).
8. A stimulus appears on the Far Zone of the virtual space located at the point of intersection between this zone and the resting gaze vector $D_R$. The stimulus can be a flying object such as a bird, an insect, a drone, etc.
9. The stimulus moves over the Far Zone following a predetermined path with a homogeneous time distribution in all its portions. The linear velocity of the stimulus will be set between 0.2 m/s and 0.6 m/s, preferably 0.4 m/s. The virtual reality device records eye and head movements as the patient follows the stimulus with his/her gaze.
10. At the end of the path established over the Far Zone, the stimulus moves to the Near Zone and makes a path analogous to that of the Far Zone, covering the same opening angle and at an equivalent angular speed. The virtual reality device records eye and head movements.
11. End of test and registration.
12. The device calculates and shows the gaze dynamics map in each plane to the patient.

Figure 3:
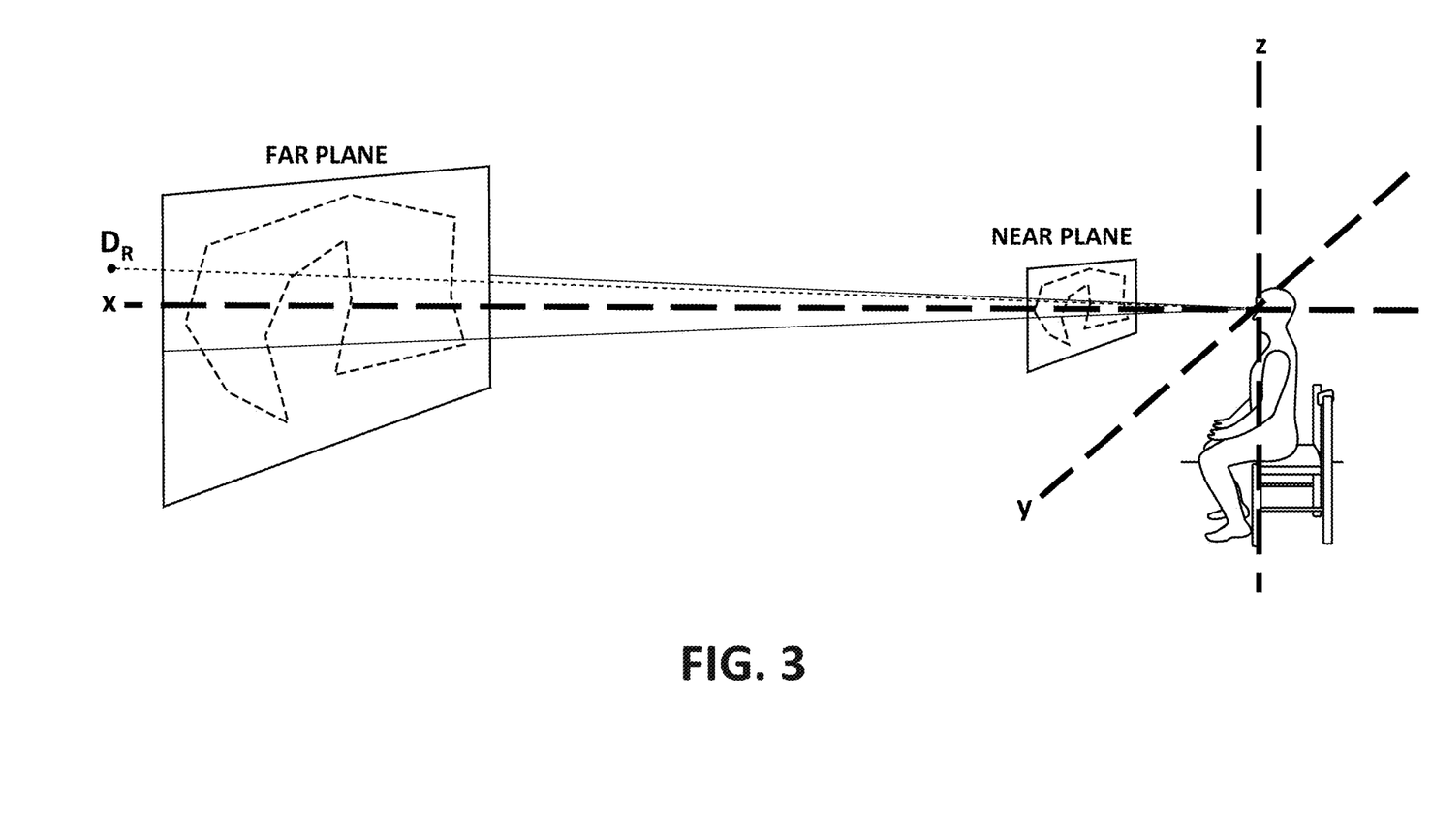
FIG. 3: diagram of the test where the position of the user is seen with respect to the coordinate system, and the two planes with the stimulus path, in dashed line. $D_R$ is the gaze point of rest.

With the recording of head and eye movements in each plane (FIG. 3), a map of frequency of use of the lens plane can be calculated when the stimulus is in the far plane and another map when it is in the near plane.

Figure 4:
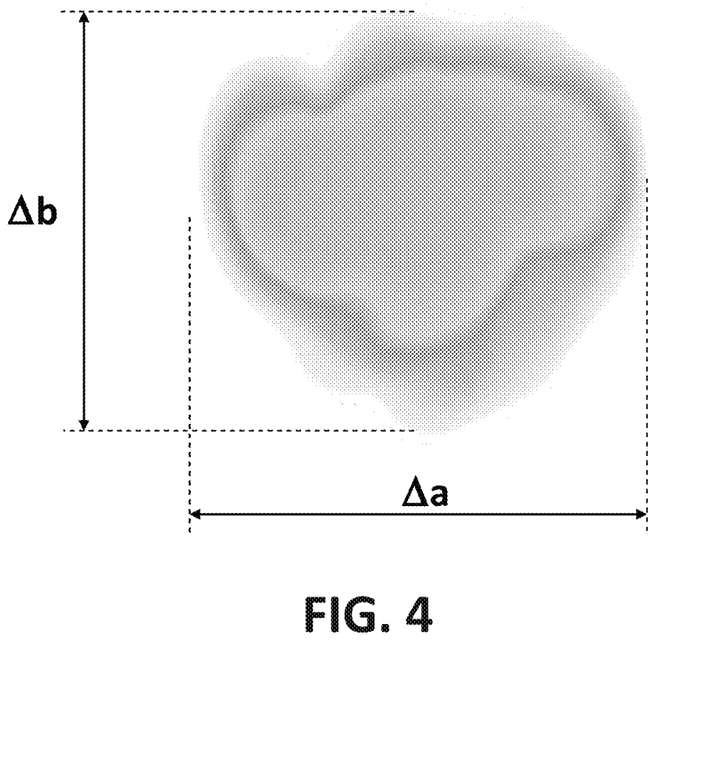
FIG. 4: graphic representation of the vertical and horizontal amplitudes Δa and Δb of a gaze dynamics map. The different intensities of gray show the values of frequency of use.

Consequently, two gaze dynamics or frequency of use maps will be generated, one for each distance. The following parameters will be extracted from each of these maps (FIGS. 4 and 5):

$\Delta a_L$: maximum horizontal amplitude of the far map in degrees (FIG. 4).

$\Delta b_L$: maximum vertical amplitude of the far map in degrees (FIG. 4).

$\Delta ab_L$: average value in degrees of the maximum horizontal amplitude $\Delta a_L$ and maximum vertical amplitude $\Delta b_L$ of the far map.

$\Delta a_C$: maximum horizontal amplitude of the near map in degrees (FIG. 4).

$\Delta b_C$: maximum vertical amplitude of the near map in degrees (FIG. 4).

$\Delta ab_C$: average value in degrees of the maximum horizontal amplitude $\Delta a_C$ and maximum vertical amplitude $\Delta b_C$ of the near map.

$PM_L$: point of maximum frequency of use of the lens plane when the stimulus is in the far plane. If there is more than one point with the same maximum frequency value, a point having as horizontal coordinate the average of the horizontal coordinates of the maximum points found, and as vertical coordinate the average of the vertical coordinates of the maximum points found (FIG. 5).

$PM_C$: point of maximum frequency of use of the lens plane when the stimulus is in the near plane. In the event that there is more than one point with the same value of maximum frequency, a point having as horizontal coordinate the average of the horizontal coordinates of the maximum points found, and as vertical coordinate the average of the vertical coordinates of the maximum points found (FIG. 5).

Figure 5:
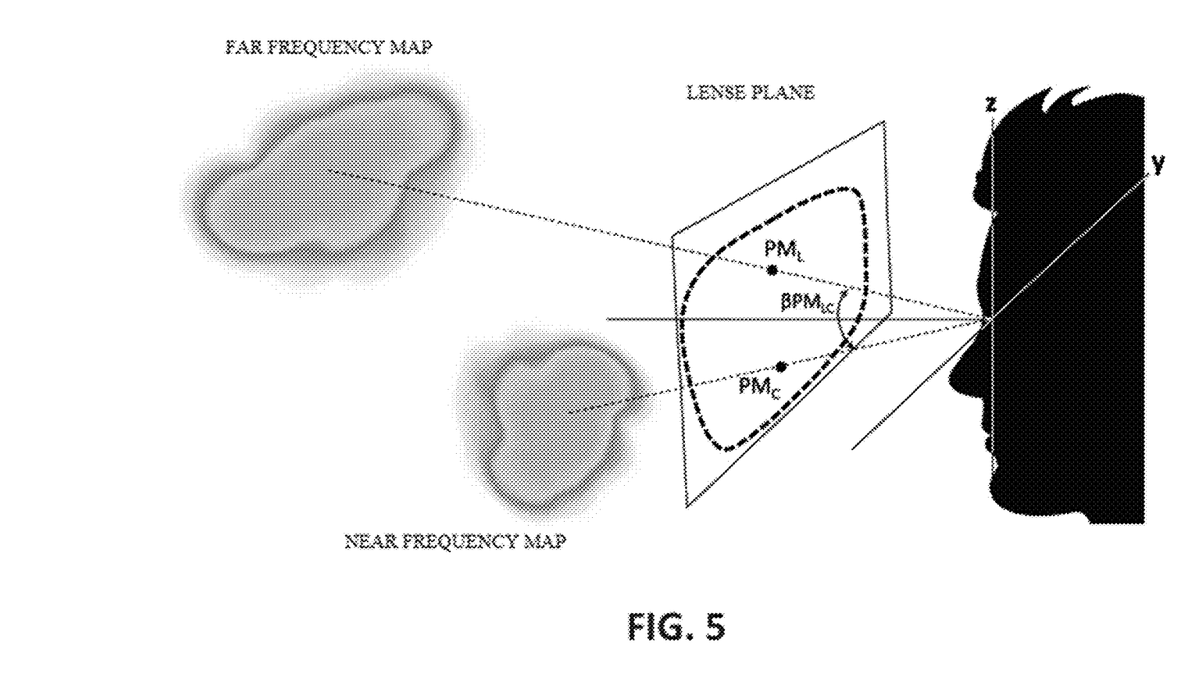
FIG. 5: diagram of the relative position of the frequency maps and the points ($PM_L$ y $PM_C$) of maximum frequency in far and near projected on the plane of the lens, as well as the angle ($\beta PM_{LC}$) formed by these two points with respect to the coordinates origin.

$\beta PM_{LC}$: angle formed by $PM_L$ y $PM_C$ points with the origin of coordinates (FIG. 5).

Thus, a total of 9 parameters are obtained for each user. The areas of a progressive lens are defined as:

$A_I$ (intermediate vision area or "intermediate vision clear zone"): area in mm2 in the intermediate zone where the value of astigmatism is less than 0.50, and the value of the mean power is greater than +0.25 D of the far target power value and the average power value is less than 85% of the target value of the addition.

The size of the intermediate vision area ($A_I$) in mm2 of the progressive lens will be determined from the angle formed by the $PM_L$ and $PM_C$ points with the origin of coordinates ($\beta PM_{LC}$), expressed in degrees (°), following a linear relationship for $\beta PM_{LC}$ values between 0° and 18° according to the following relationship:

$$A_I = m \times \beta PM_{LC} + n$$

wherein m has values between 0.5 mm²/° and 1.5 mm²/°, preferably 1.0 mm²/° and n has values between 15 mm² and 30 mm², preferably 23 mm².

$A_L$ (far vision area or "far vision clear zone"): area in mm² in the far zone where the astigmatism value is less than 0.50 D and the mean power value is less than +0.25 D of the target far power value. In the upper part, the area limits 8 mm above the pupil position (known as the fitting cross or segment). The lower part limits 4 mm below the pupil at the point known as PRP.

The size of the far vision area ($A_L$) in mm2 of the progressive lens will be determined from the average of the maximum horizontal and vertical amplitude of the gaze dynamics map in the far plane ($\Delta ab_L$), expressed in degrees (°), following a linear relationship for $\Delta ab_L$ values between 10° and 80° according to the following relationship:

$$A_L = i \times \Delta ab_L + j$$

Wherein i values are between 1.0 mm²/° and 1.4 mm²/°, preferably 1.2 mm²/° and j values are between 120 mm² and 160 mm², preferably 140 mm².

$A_C$ (near vision area or "near vision clear zone"): area in mm² in the near zone where the astigmatism value is less than 0.50 D and the mean power value is greater than 85% of the target value of addition. At the bottom, the area limits 2 mm below the near reference point (known as the Near Reference Point or NRP).

The size of the near vision area ($A_C$) in mm² of the progressive lens will be determined from the average of the maximum horizontal and vertical amplitude of the gaze dynamics map in the near plane ($\Delta ab_C$), expressed in degrees (°), following a linear relationship for $\Delta ab_c$ values between 10° and 80° according to the following relationship:

$$A_C = k \times \Delta ab_C + l$$

wherein k values are between 0.15 mm²/° and 0.25 mm²/°, preferably 0.20 mm²/° and where l values are between 20 mm² and 30 mm², preferably 25 mm².

By virtue of the method of the invention it is possible to design a lens whose areas are specially adapted to the dynamics of the users gaze.

In view of this description and figures, the person skilled in the art will be able to understand that the invention has been described according to some preferred embodiments thereof, but that multiple variations can be introduced in said preferred embodiments, without exceeding the object of the invention as claimed.

The invention claimed is:

1. A method to establish the size of the zones of the near $A_C$, far $A_L$ and intermediate $A_I$ vision of a progressive lens, wherein the method comprises the following steps:

a. generating a gaze map through the use of virtual reality in a near plane and a distant plane;
b. calculating a maximum horizontal amplitude of each map in degrees, $\Delta a_L$, $\Delta a_C$;
c. calculating a maximum vertical amplitude of each map in degrees $\Delta b_L$, $\Delta b_C$;
d. determining the size of the far vision area $A_L$ in mm² from an average of the maximum horizontal and vertical amplitude in the far plane ($\Delta ab_L$) following a linear relationship whose result for $\Delta ab_L$ values between 10° and 80° is obtained according to the following relationship:

$$A_L = i \times \Delta ab_L + j,$$

wherein I has values between 1.0 mm²/° and 1.4 mm²/° and j has values between 120 mm² and 160 mm²;
wherein $A_L$ is the area in mm² in the far zone where the astigmatism value is less than 0.50D and the mean power value is less than +0.25D of a target far power value; said area $A_L$ limiting, in its upper part, 8 mm above the position of the pupil, and, in its lower part, 4 mm below the position of the pupil;

e. determining the size of the near vision area ($A_C$) in mm² from the average of the maximum amplitude in horizontal and vertical in the near plane ($\Delta ab_C$) following a linear relationship whose result for values of $\Delta ab_C$ between 10° and 80° is obtained according to the following relationship:

$$A_C = k \times \Delta ab_C + l,$$

wherein k has values between 0.15 mm²/° and 0.25 mm²/° and wherein l has values between 20 mm² and 30 mm²;
wherein $A_C$ is the area in mm² in the near zone where the astigmatism value is less than 0.50D and the mean power value is greater than 85% of a target value of addition; said area $A_C$ limiting, at the bottom, 2 mm below the point known as the near reference point;

f. determining the size of the intermediate vision area $A_I$ in mm² from the angle $\beta PM_{LC}$ formed by:
the points of maximum frequency of use in each of the far and near planes, $PM_L$ and $PM_C$, or, when there is more than one point with the same maximum frequency value per plane, a respective point having as horizontal coordinate the average of the horizontal coordinates of the maximum points found, and as vertical coordinate the average of the vertical coordinates of the maximum points found,
with respect to the origin of coordinates following a linear relation whose result for $\beta PM_{LC}$ values between 0° and 18° is obtained according to the following relationship:

$$A_I = m \times \beta PM_{LC} + n$$

wherein m has values between 0.5 mm²/° and 1.5 mm²/° and n has values between 15 mm² and 30 mm²;
wherein $A_I$ is the area in mm² in the intermediate zone where the value of astigmatism is less than 0.50D, and the value of the mean power is greater than +0.25D of the far target power value and the average power value is less than 85% of the target value of the addition;
wherein said origin of coordinates is the origin (0,0,0) of a Cartesian coordinate system at the midpoint of a vector joining the user's pupils, wherein the xy plane is defined parallel to the ground and the z axis perpendicular to the ground; and
wherein steps b-f are performed by a processor.

2. The method according to claim 1, wherein i has a value of 1.2 mm$^2$/° and j has a value of 140 mm$^2$.

3. The method according to claim 1, wherein k has a value of 0.02 mm$^2$/° and l has a value of 25 mm$^2$.

4. The method according to claim 1, wherein m has a value of 1.0 mm$^2$/° and n has a value of 23 mm$^2$.

5. A method for manufacturing a progressive lens, the method comprising delimiting the size of the areas of the near $A_C$, far $A_L$ and intermediate $A_I$ vision zones, wherein said size is calculated according to the method of claim 1.

6. A non-transitory computer program product comprising program code which, when loaded into a processor, causes said program code to execute the method of claim 1.

\* \* \* \* \*